US008529954B2

(12) United States Patent
Lebon et al.

(10) Patent No.: US 8,529,954 B2
(45) Date of Patent: Sep. 10, 2013

(54) COMPOSITION BASED ON GAMMA-HYDROXYBUTYRIC ACID

(75) Inventors: Christophe Lebon, Rouvres (FR); Pascal Suplie, Montaure (FR)

(73) Assignee: Debregeas et Associes Pharma, Paris (FR)

( * ) Notice: Subject to any disclaimer, the term of this patent is extended or adjusted under 35 U.S.C. 154(b) by 0 days.

(21) Appl. No.: 13/129,130

(22) PCT Filed: Nov. 10, 2009

(86) PCT No.: PCT/FR2009/052169
§ 371 (c)(1),
(2), (4) Date: Aug. 3, 2011

(87) PCT Pub. No.: WO2010/055260
PCT Pub. Date: May 20, 2010

(65) Prior Publication Data
US 2011/0293729 A1    Dec. 1, 2011

(30) Foreign Application Priority Data

Nov. 14, 2008  (FR) ..................................... 08 57763

(51) Int. Cl.
*A61K 9/16* (2006.01)
*A61K 9/50* (2006.01)
(52) U.S. Cl.
USPC ............................. 424/494; 424/490; 424/493
(58) Field of Classification Search
USPC ........................................................ 424/494
See application file for complete search history.

(56) References Cited

U.S. PATENT DOCUMENTS

| | | | |
|---|---|---|---|
| 4,101,650 A | 7/1978 | Umezawa | |
| 4,424,235 A | 1/1984 | Sheth et al. | |
| 5,846,971 A | 12/1998 | Sangekar et al. | |
| 6,214,386 B1 | 4/2001 | Santus et al. | |
| 6,264,989 B1 * | 7/2001 | Kato et al. | 424/490 |
| 6,436,438 B1 * | 8/2002 | Momberger et al. | 424/458 |
| 7,815,934 B2 * | 10/2010 | Boehm | 424/451 |
| 2003/0064099 A1 | 4/2003 | Oshlack et al. | |
| 2005/0214372 A1 | 9/2005 | Di Capua et al. | |
| 2006/0210630 A1 | 9/2006 | Liang et al. | |
| 2007/0092565 A1 | 4/2007 | Aurora et al. | |
| 2007/0270491 A1 | 11/2007 | Cook et al. | |
| 2008/0081068 A1 | 4/2008 | Oberegger et al. | |
| 2012/0164228 A1 | 6/2012 | Suplie et al. | |
| 2012/0207843 A1 | 8/2012 | Lebon et al. | |

FOREIGN PATENT DOCUMENTS

| | | |
|---|---|---|
| EP | 0344704 | 12/1989 |
| EP | 0635265 | 1/1995 |
| EP | 1 293 209 A1 | 3/2003 |
| FR | 2 829 932 A1 | 3/2003 |
| GB | 2 331 702 A | 6/1999 |
| WO | WO9300083 | 1/1993 |
| WO | WO 00/66089 A1 | 11/2000 |
| WO | WO 01/10417 A1 | 2/2001 |
| WO | WO 01/80822 A2 | 11/2001 |
| WO | WO 02/085336 A1 | 10/2002 |
| WO | WO 03/013479 A1 | 2/2003 |
| WO | WO 03/026621 A2 | 4/2003 |
| WO | WO 2005/079760 A1 | 9/2005 |
| WO | WO 2005/101983 A2 | 11/2005 |

OTHER PUBLICATIONS

PCT/FR2009/052169: International Search Report in English and French, dated Jan. 15, 2010 (6 pages).
PCT/FR2009/052169: Opinion Escrite Sur La Brevetabilite de L'invention, Institut National de la Properiete Industrielle, 6 pages (undated).
PCT/FR2009/052169: Rapport de Recherche Preliminaire Patel, Institut National de la Properiete Industrielle, 7 pages, Jan. 15, 2010.
Mar. 30, 2011 International Search Report issued in International Patent Application No. PCT/FR2010/051691 (with English Translation).
Rouge et al., "Buoyancy and Drug Release Patterns of Floating Minitablets Containing Piretanide and Atenolol as Model Drugs," *Pharmaceutical Development and Technology*, vol. 3, No. 1, pp. 73-84, 1998.
Elkheshen et al., "In vitro and in vivo Evaluation of Floating Controlled Release Dosage Forms of Verapamil Hydrochloride," *Pharmazeutische Industrie*, vol. 66, No. 11, pp. 1364-1372, 2004.
Sawicki et al., "Compressibility of floating pellets with verapamil hydrochloride coated with dispersion Kollicoat SR 30 D," *European Journal of Pharmaceutics and Biopharmaceutics*, vol. 60, pp. 153-158, 2005.
Sauzet et al., "An innovative floating gastro retentive dosage system: Formulation and in vitro evaluation," *International Journal of Pharmaceutics*, vol. 378, pp. 23-29, 2009.
Goole et al., "Development and evaluation of new multiple-unit levodopa sustained-release floating dosage forms," *International Journal of Pharmaceutics*, vol. 334, pp. 35-41, 2007.
Feb. 14, 2013 Office Action issued in U.S. Appl. No. 13/390,213.
Feb. 3, 2011 International search Report issued in International Patent Application No. PCT/FR2010/051697.
Mar. 13, 2012 International Preliminary Report on Patentability issued in International Patent Application No. PCT/FR2010/051697.

\* cited by examiner

*Primary Examiner* — Robert T Crow
*Assistant Examiner* — Doan Phan
(74) *Attorney, Agent, or Firm* — Oliff & Berridge, PLC

(57) ABSTRACT

The present invention relates to a granule of gamma-hydroxybutyric acid or of one of its pharmaceutically acceptable salts, characterized in that it comprises a solid core on which the gamma-hydroxybutyric acid or one of its salts is supported.

18 Claims, No Drawings

COMPOSITION BASED ON GAMMA-HYDROXYBUTYRIC ACID

CROSS-REFERENCE TO RELATED APPLICATIONS

This application is a national phase application of PCT/FR2009/052169 filed on Nov. 10, 2009 and claims priority to French Application No. 0857763 filed on Nov. 14, 2008. The PCT published as WO2010/055260 on May 20, 2010. The above-identified patent applications are incorporated herein, by reference, in their entirety.

FIELD OF THE INVENTION

The present invention relates to a novel composition based on gamma-hydroxybutyric acid or one of its pharmaceutically acceptable salts, as well as the method of preparation of the aforementioned composition.

BACKGROUND OF THE INVENTION

Gamma-hydroxybutyric acid (or GHB) is regarded as an endogenous neuromodulator or neurotransmitter present in the human brain. It is a metabolite of Gamma-aminobutyric acid (GABA).

Thus the medicament Xyrem® comprising as active constituent a sodium salt of GHB, namely sodium hydroxybutyrate (or sodium oxybate, Na-GHB), is used for the treatment of narcolepsy in adult patients exhibiting cataplexy.

GHB is also used as an anaesthetic.

It also has an alcohol-mimetic effect on the central nervous system. Thus clinical studies have already shown the effectiveness of GHB in the treatment of alcohol dependency.

However, the major drawback of GHB in terms of effectiveness is linked to its pharmacokinetic profile. For GHB has a short half life, a high plasma concentration peak, with fast elimination and variable (low) bioavailability as a function of feeding. For example, it is known that sodium hydroxybutyrate is absorbed very quickly by the gastroenteric system with a maximum peak of approximately 30-45 minutes after its administration and that it has a half life of approximately 20-25 minutes. Moreover, it is eliminated very quickly (in approximately 4 to 5 hours).

This pharmacokinetic profile therefore involves the administration of a substantial daily dose of 4 to 9 g, in doses repeated every 3 to 4 hours, and in particular in the middle of the night for narcoleptic patients, which results in a limited effectiveness due to the wide variations in plasma concentration as well as a risk of intolerance due to these same variations.

The existing galenic forms do not allow this profile to be improved.

For example, oral solutions are restrictive in terms of observance and can give rise to problems of stability and preservation. Moreover, since GHB is unstable in an acidic environment it is not possible to exclude the possibility of degradation of the GHB in the gastric environment and therefore a reduction of the bioavailability.

SUMMARY OF THE INVENTION

The object of the present invention is to provide a novel galenic form based on gamma-hydroxybutyric acid or one of its salts (in particular sodium) which makes it possible to circumvent the aforementioned drawbacks.

Thus an object of the present invention is to provide a novel galenic form based on gamma-hydroxybutyric acid or one of its salts which makes it possible to reduce the daily dose and the number of times it is taken per day, increasing the apparent half life and the bioavailability of the active constituent.

Thus an object of the present invention is to provide a novel galenic form based on gamma-hydroxybutyric acid or one of its salts which makes it possible to reduce or eliminate the secondary effects by reducing the plasma concentrations used.

Thus an object of the present invention is to provide a novel galenic form based on gamma-hydroxybutyric acid or one of its salts which makes it possible to improve the patient's comfort and the monitoring of the treatment by reducing the number of daily doses, in particular avoiding taking them at night.

Thus an object of the present invention is to provide a novel galenic form based on gamma-hydroxybutyric acid or one of its salts which makes it possible to improve the safety of the product by a stable galenic form and which avoids or reduces the diversions of use.

DETAILED DESCRIPTION OF THE INVENTION

The present invention relates to a granulate of gamma-hydroxybutyric acid or one of its pharmaceutically acceptable salts, characterised in that it comprises a solid core on which is supported the gamma-hydroxybutyric acid or one of its salts.

The active constituent used is preferably in the form of salt, and more particularly in the form of sodium salt (sodium salt of 4-hydroxybutyric acid or sodium oxybate).

The expression "granulate" designates a preparation consisting of dry solid grains, each forming an aggregate of powder particles having sufficient solidity to allow various manipulations.

Granulates are generally present in the form of small grains of irregular angular shape. The granulates according to the present invention have the characteristic that they have a shape which is quite regular, homogeneous and quasi-spherical.

From the physical point of view the granulates are aggregates of various crystallised or amorphous powder particles.

The granulates according to the present invention are intended for oral administration, and more particularly intended to be swallowed just as they are.

The granulates according to the present invention have a characteristic structure of the core/shell type, wherein the core is of a different nature from the active constituents which form the shell.

According to a particular embodiment, the core of the granulates may however comprise particles of gamma-hydroxybutyric acid or one of its salts.

Thus these granulates have a multi-layer structure. For the active constituent (gamma-hydroxybutyric acid or one of its salts) is deposited on the core and therefore forms a layer (or shell) deposited around this core (or support).

The core of the granulates may also be regarded as being a support on which the particles of the active constituent become fixed.

The core consists of solid particles and the active constituent supported by the said core is also in solid form.

Therefore the present invention is based on the development of a novel oral multi-particle form.

Thus the original feature of the form presented here consists of a granulate intended for oral administration, enabling the administration of gamma-hydroxybutyric acid or one of its salts in sufficiently substantial doses to require only one or two administrations per day, the granulate according to the invention being highly concentrated in active constituent.

The granulates according to the present invention have the advantage of enabling a reduction, for the patient, of the number of daily doses.

According to a preferred embodiment, the core of the granulates according to the invention consists of particles of a compound chosen from amongst the group consisting of polyols such as mannitol, sorbitol, maltitol or xylitol, lactose, dicalcium phosphate, carbonates such as calcium carbonate, potassium carbonate, magnesium carbonate or sodium carbonate, gluconates, silicates, in particular magnesium amino silicate (Neusilin®), sugar crystals, saccharose, silica derivatives and starch derivatives.

According to a particularly preferred embodiment the core of the granulates according to the invention consists of mannitol. Preferably, the core of the granulates does not consist of neutral core.

Therefore the present invention preferably relates to granulates comprising gamma-hydroxybutyric acid (or one of its salts) deposited on a core consisting of particles of mannitol.

According to a particularly advantageous embodiment, the core of the granulates according to the present invention does not include a cellulose compound.

According to a preferred embodiment, the aforementioned granulates also include a binder.

The role of the binder is to bind the particles to one another, that is to say to perfect the cohesion of the granulate. Thus the binders make it possible to ensure good cohesion of the active constituent and the core in the granulates.

Thus the binders, like the active constituent, are deposited around the core of the granulates.

As binders, mention may be made of the majority of hydrophilic excipients which give viscous solutions: gum arabic and gum tragacanth, methylcellulose and carboxymethylcellulose, gelatin, starches, maltodextrins, PEG 4000 and 6000 in alcohol solution, polyvidone in aqueous or alcohol solution, and also saccharose, glucose or sorbitol solutions.

The binders of the granulates according to the invention are preferably chosen from amongst the group consisting of starch, saccharose, gum arabic, polyvinylpyrrolidone (PVP or polyvidone), hydroxypropylmethylcellulose (HPMC), shellac, hydroxypropylcellulose (HPC), cellulose, polyols or alginates, polyglycolysed glycerides (Gelucire®) or macrogolglycerides, in particular stearoyl macrogolglycerides, also acrylic derivatives, as well as mixtures thereof.

Amongst the polyols mention may be made in particular of mannitol, sorbitol, maltitol or xylitol.

According to a particular embodiment, the binders used in the granulates according to the present invention are not cellulose compounds. They are therefore preferably chosen from amongst the group consisting of polyvinylpyrrolidone, shellac, polyols or alginates, polyglycolysed glycerides (Gelucire®) or macrogolglycerides, in particular stearoyl macrogolglycerides, as well as mixtures thereof.

Use may also be made of a binder chosen from amongst the groups referred to above for particular properties; for example it may be useful to use pH-dependent excipients such as EUDRAGIT® L100 or shellac as binder. Use of polyglycolysed glycerides (Gelucire®) may also be preferred for their hydrophobic character.

According to a preferred embodiment the granulates according to the invention are coated.

The coated granulates consist of grains coated with one or more layers of mixtures of various excipients.

Thus the preferred coated granulates according to the present invention comprise the active constituent deposited on a core consisting of particles of mannitol, as well as an additional layer consisting of the coating agent.

According to a preferred embodiment the granulates according to the invention have a multi-layer structure and consist of a core, preferably based on mannitol, on which are deposited the active constituent (GHB) and the binder which are themselves coated with one or more layers of coating agent(s).

The granulates according to the invention are preferably coated with a coating agent chosen from amongst the group consisting of shellac, polyvinylpyrrolidone, polyethylene glycol (PEG), cellulose derivatives such as HPMC or HPC, saccharose, alginate, glycerides of fatty acids and methacrylic polymers.

According to a particularly preferred embodiment, the granulates according to the invention are coated with shellac.

The granulates according to the invention may also be coated with a coating film which includes one or more excipients such as lubricants, colourings, sweeteners, plasticisers or anti-blocking agents.

The granulates according to the invention may also include an enteric coating for gastric protection. Such granulates are therefore gastro-resistant.

Such a coating is obtained using coating agents consisting in particular of HPMCP (hydroxypropylmethylcellulose phthalate-hypromellose phthalate) or methacrylic polymers, in particular Eudragit® L, or shellac.

The presence of this enteric coating may influence the bioavailability of the active constituent (GHB or Na-GHB), in particular avoiding degradation thereof in an acidic environment.

The granulates according to the invention may also include a sustained-release coating.

Such granulates enable a modified or delayed release of the active constituents (modified-release granulates).

Such a coating is obtained using coating agents consisting in particular of copolymers of methacrylates and acrylates, Eudragit® S100, shellac, cellulose derivatives, in particular ethylcellulose, and acrylic derivatives.

The presence of this modified-release coating influences in particular the apparent half life of the active constituent (in particular GHB or Na-GHB).

The granulates according to the present invention may also include a lubricant and/or a flavouring and/or a sweetener and/or a colouring.

Amongst the lubricants used within the context of the present invention mention may be made in particular of talc, magnesium stearate, silica derivatives (in particular Aerosil®) or waxes.

Amongst the flavourings used within the context of the present invention, mention may be made of the flavourings conventionally used in food additives.

The sweeteners used within the context of the present invention are in particular those listed in the directive 94/35/EC of 30 Jun. 1994 concerning sweeteners intended for use in foodstuffs (modified by the directive 2006/25/EC of 5 Jul. 2006). Thus mention may be made in particular of aspartame E951, sorbitol E420, mannitol E421, acesulfame-K E950 or saccharine E954.

The colourings used within the context of the present invention are in particular those listed in the directive 95/45/EC of 26 Jul. 1995 concerning colourings which can be used in foodstuffs (modified by the directive 2006/33/EC of 20 Mar. 2006). Thus mention may be made in particular of the colourings E100 to E180.

In order to avoid unintentional intake of GHB within the context of diverted uses, it is particularly worthwhile to incorporate into the granulates according to the invention a colouring which is released if the said granulate is dissolved or crushed.

Insoluble excipients may also be used in the formulation of the granulate in order to avoid the total solubilisation of the granulate for diverted and malicious use.

The granulates according to the invention may also contain one or more plasticisers such as those conventionally used by the person skilled in the art.

A granulate according to the present invention preferably comprises at least 35% by weight of gamma-hydroxybutyric acid or one of its salts, and preferably at least 45% by weight of gamma-hydroxybutyric acid or one of its salts.

According to another preferred embodiment, the granulates according to the present invention comprise from 35% to 65% by weight of gamma-hydroxybutyric acid or one of its salts.

Moreover, the core of a granulate according to the invention preferably represents from 20% to 80%, more preferably from 30% to 55%, even from 35% to 55% by weight relative to the total weight of the said granulate.

The granulates according to the invention preferably comprise from 0 to 10%, and preferably from 4 to 8%, by weight of binder.

The granulates according to the invention preferably comprise from 10% to 45%, and preferably from 20% to 30%, by weight of coating agent.

The granulates according to the invention preferably comprise less than 3% by weight of flavouring.

The granulates according to the invention preferably comprise less than 2% by weight of colouring.

The granulates according to the invention preferably comprise less than 1.5% by weight of sweetener.

The granulates according to the invention preferably comprise less than 4% by weight of lubricant.

The granulates according to the invention may also include a plasticiser, in particular triethylcitrate, in a proportion of less than 3% by weight.

The present invention also relates to a pharmaceutical composition, comprising granulates as defined above.

The present invention also relates to the granulates according to the invention as defined above for use in the treatment of catalepsy in narcoleptic patients.

The present invention also relates to the granulates according to the invention as defined above for use in weaning from alcohol.

The granulates according to the invention may be packaged in individual containers, for example in sachets, sticks, paper bags or bottles, and preferably in plastic ampoules.

The granulates according to the present invention have the advantage of reducing the number of daily doses. Thus since the granulates according to the invention contain high doses the quantity of γ-hydroxybutyric acid (or one of its salts) per unit dose (that is to say per individual container containing the granulates, in particular a plastic ampoule) is preferably greater than or equal to 500 mg, advantageously greater than or equal to 1 g, and preferably greater than or equal to 1.5 g.

The granulates according to the present invention may be ingested directly or may be dispersed in a solution, or mixed in a dietary support such as a yoghurt or a compote.

The present invention also relates to a method of preparation of a granulate as defined above, characterised in that it comprises a step of application by powdering of the gamma-hydroxybutyric acid or one of its salts on a solid particulate support.

The method of the invention therefore consists of mixing the active constituent gamma-hydroxybutyric acid (or one of its salts) in the form of powder in the presence of solid particles as support. Thus the solid particles of the support used form a core on which the particles of the active constituent are deposited.

The structure of the granulates according to the invention is therefore linked to the implementation of this particular method which makes it possible to obtain granulates with a core/skin structure.

By carrying out comparative tests of preparation of granulates by a method of direct granulation with different excipients usually used in granulation, it was found that the results obtained concerning the granulate itself are satisfactory with regard to the appearance, friability and dissolution. However, the granulates obtained by such a method have a very high specific surface area necessitating substantial quantities of coating polymers according to the techniques which are conventionally used.

Thus the granulates of the present invention are characterised in that they have a low specific surface area. Moreover, in appearance they are relatively smooth and have a quite regular shape.

The aforementioned step of powdering of the method for preparation of the granulates according to the invention may also include a step of spraying of an alcoholic or hydroalcoholic or aqueous solution of a binder.

This step of spraying and the step of powdering are preferably carried out simultaneously or alternately.

The aforementioned step of powdering is preferably carried out simultaneously with a step of spraying of a binder in the form of a solution.

The combination of these steps makes it possible to ensure good cohesion of the active constituent on the core of the granulates.

Thus an advantageous implementation of the method according to the invention consists of applying the active constituent in the form of powder on the aforementioned particulate support (or core of the granulates) by alternating the sequences of spraying of the binder in the form of a solution.

The method according to the invention may also include, after the step of powdering, one or more steps of coating of the granulate, in particular by depositing the coating agent(s) in the form of films on the granulate by lamination.

Thus the small specific surface area of the granulates according to the invention makes it possible, in the case of coating, to reduce the quantity of coating agent used and therefore to dilute the active constituent less in the said coated granulates.

A preferred embodiment of the method according to the invention consists of a method including, after the step of coating, a step of mixing with a lubricant and/or a flavouring and/or a sweetener and/or a colouring, which may themselves be prepared in the form of granulates in order to be finally mixed with the active granulates.

However, the lubricants, flavourings, sweeteners and colourings may also be added before the aforementioned step of powdering.

If necessary, the aforementioned method may also include, before the step of powdering, a step of crushing of the active constituent (GHB) in the presence of a diluent.

When the method includes a step of crushing, this may be followed by a step of addition of lubricants, flavourings, sweeteners and colourings.

Thus according to a preferred embodiment the method of preparation of the granulates according to the invention comprises the following steps:
- a step of application of γ-hydroxybutyric acid (or one of its pharmaceutically acceptable salts), mixed with at least one diluent, by powdering on a solid particulate support, combined with a step of spraying of an alcoholic or hydroalcoholic solution of a binder, in order to obtain a granulate, the said granulate consisting of a core corresponding to the aforementioned support on which particles of the active constituent are deposited;
- one or more steps of coating of the granulate obtained in the preceding step by deposition of the coating films by lamination, in order to obtain a coated granulate; and
- an optional step of mixing with a lubricant and/or a flavouring and/or a sweetener and/or a colouring, which may or may not be in the form of granulate.

EXAMPLES

Example 1

Detailed Description of a Preferred Embodiment of Preparation of Granulates The ingredients are weighed one by one, then the active constituent is introduced into a cubic mixer. The quantity of diluent is weighed in its turn (mannitol 160) and introduced into the mixer. The mixer is then set in operation. The mixture obtained (A) is satisfactory after 10 minutes.

The mixture is then introduced into a Forplex FLO mill and all of the mixture is crushed in such a way as to reduce the particle size of the whole (active constituent+diluent). This makes it possible to increase the difference in size of the particles of mannitol (support) (approximately 300µ) and of the crushed mixture (less than 100µ and preferably 25µ).

The following step of the method is a step of powdering in which the equipment used is a conventional turbine.

Thus the mannitol which serves as support is introduced into a vessel, this latter is then set in rotation (approximately 20 rotations per minute) and the mixture A is deposited by sequential powdering on the mannitol support, alternating with phases of spraying of the binder solution (PVP/HPMC/OH/H$_2$O).

This step is carried out sequentially in order to enable the evaporation and the drying of the granulates.

At the end of the step of powdering, a drying phase is carried out in order to cause hot air at approximately 40° C. to circulate over the mass of granulates for approximately 14 hours.

At the end of the drying step the product is sieved in such a way as to select the particles obtained. The mixture is then returned to the vessel.

The following step is the step of coating. The solutions (or suspensions) containing the coating agents are placed successively in a low-pressure vessel subjected to agitation. The mass of granulates obtained is then placed in the vessel of a fluidised-air bed and the coating solutions are then sprayed successively in a continuous manner onto the granulates. Steps of drying/coating may also be carried out.

An apparatus of the fluidised-air bed type (or similar technology) is preferably used for the step of coating due to its great effectiveness in terms of evaporation, which makes it possible to considerably reduce the coating time.

Different types of coating may also be produced which each play a particular role, namely: consolidation, production of a hydrophobic layer, colouring, bitterisation, modification of the release of the active constituent . . . .

Afterwards, the additives such as sweeteners, lubricants, flavourings and colourings which may or may not be in the form of granulates may be added to the granulates in a mixer.

The last step consists of distributing the granulates into individual packages such as plastic ampoules or sachets.

The following tables describe examples of granulates obtained within the context of the present invention.

Examples 2 to 6

Preparation of Granulates According to the Invention

| FORMULA N° 1 | | |
| --- | --- | --- |
| Designation | Function | Formulae Percentage (%) |
| GHB | Active constituent | 48.6 |
| Eudragit ® L100 | Binder | 3.12 |
| saccharose | Core (support) | 20.77 |
| Aspartame | Sweetener | 0.15 |
| Shellac | Coating | 19.23 |
| Neusilin ® (Seppic) | Diluent | 4.22 |
| Talc | Lubricant | 3.85 |
| Colouring | Colouring | 0.06 |
| TOTAL | | 100.00 |

| FORMULA N° 2 | | |
| --- | --- | --- |
| Designation | Function | Formulae Percentage (%) |
| GHB | Active constituent | 34.57 |
| PVP | Binder | 5.00 |
| Gelucire (Gattefossé) | Diluent | 10.00 |
| Neusilin ® (Seppic) | Support | 21.79 |
| Hypromellose | Pre-coating | 2.00 |
| Eudragit ® L30D | Coating | 21.89 |
| Triethylcitrate | Plasticiser | 2.19 |
| Talc | Lubricant | 2.50 |
| Colouring | Colouring | 0.06 |
| TOTAL | | 100.00 |

| FORMULA N° 3 | | |
| --- | --- | --- |
| Designation | Function | Formulae Percentage (%) |
| GHB | Active constituent | 45.09 |
| PVP | Binder | 4.51 |
| Calcium Carbonate | Support/buffer | 10.48 |
| Mannitol | Support (core) | 11.27 |
| Hypromellose | Pre-coating | 2.00 |
| Hypromellose Phthalate | Coating | 21.89 |
| Triethylcitrate | Plasticiser | 2.19 |
| Talc | Lubricant | 2.50 |
| Colouring | Colouring | 0.06 |
| TOTAL | | 100.00 |

| FORMULA N° 4 | | |
|---|---|---|
| Designation | Function | Formulae Percentage (%) |
| GHB | Active constituent | 48.6 |
| EUD L100 | Binder | 2.9 |
| saccharose | Support (core) | 20.83 |
| Neusilin ® (Seppic) | diluent | 4.37 |
| Eudragit ® L100 | Coating | 18.35 |
| Triethylcitrate | Plasticiser | 1.9 |
| Talc | Lubricant | 2.3 |
| Colouring | Colouring | 0.75 |
| TOTAL | | 100.00 |

| FORMULA N° 5 | | |
|---|---|---|
| Designation | Function | Formulae Percentage (%) |
| GHB | Active constituent | 46.33 |
| GLDB (shellac) | Binder | 4.55 |
| Mannitol | Core (support) | 19.85 |
| Neusilin ® (Seppic) | Diluent | 4.17 |
| HP55 ® (hydroxypropyl-methylcellulose phthalate) | Coating | 19.19 |
| Triethylcitrate | Plasticiser | 1.92 |
| Aspartame | Sweetener | 1.2 |
| Talc | Lubricant | 1.34 |
| Sepisperse green | Colouring | 0.5 |
| TOTAL | | 100.00 |

The invention claimed is:

1. A granulate of gamma-hydroxybutyric acid or one of its pharmaceutically acceptable salts, comprising:
   a solid core; and
   a shell layer constituted of the gamma-hydroxybutyric acid or one of its salts that is deposited around and supported by the solid core,
   wherein
      the core is of a different material than the gamma-hydroxybutyric acid or one of its salts constituting the shell layer, and
      the gamma-hydroxybutyric acid or one of its salts represents at least 35% by weight relative to a total weight of the granulate.

2. The granulate according to claim 1, wherein the material of the core is selected from the group consisting of polyols, lactose, dicalcium phosphate, carbonates, gluconates, silicates, sugar crystals, saccharose, starch derivatives and silica derivatives.

3. The granulate according claim 1, further comprising a binder deposited around the solid core.

4. The granulate according to claim 1, wherein the granulate is coated with a coating agent.

5. The granulate according to claim 1, further comprising at least one of an enteric coating or a modified-release coating.

6. The granulate according to claim 1, further comprising at least one of a lubricant, a flavoring, a sweetener or a coloring.

7. A pharmaceutical composition, comprising the granulates according to claim 1.

8. A method of preparation of the granulate according to claim 1, comprising:
   applying by powdering the gamma-hydroxybutyric acid or one of its salts on the solid core.

9. The method according to claim 8, further comprising:
   coating of the granulate, and, optionally,
   mixing the coated granulate with a lubricant and/or a flavoring and/or a sweetener and/or a coloring.

10. The granulate according to claim 2, wherein the material of the solid core includes polyols that are selected from the group consisting of mannitol, sorbitol, maltitol and xylitol.

11. The granulate according to claim 2, wherein the material of the solid core includes carbonates that are selected from the group consisting of calcium carbonate, potassium carbonate, magnesium carbonate, and sodium carbonate.

12. The granulate according to claim 3, wherein the binder is selected from the group consisting of starch, saccharose, gum arabic, polyvinylpyrrolidone, hydroxypropylmethylcellulose, shellac, hydroxypropylcellulose, cellulose, polyols, alginates, polyglycolysed glycerides and macrogolglycerides.

13. The granulate according to claim 4, wherein the coating agent is selected from the group consisting of shellac, polyvinylpyrrolidone, polyethylene glycol, cellulose derivatives, saccharose, alginate, glycerides of fatty acids and methacrylic polymers.

14. The granulate according to claim 5, wherein the granulate comprises an enteric coating, and the enteric coating consists of methacrylic polymers, shellac or hydroxypropylmethylcellulose phthalate.

15. The granulate according to claim 5, wherein the granulate comprises a modified-release coating, and the modified-release coating consists of copolymers of methacrylates and acrylates, shellac or cellulose derivatives.

16. The method according to claim 8, wherein applying by powdering of the gamma-hydroxybutyric acid or one of its salts comprises spraying of an aqueous, alcoholic or hydroalcoholic solution of a binder on the solid core.

17. The granulate according to claim 1, wherein the solid core represents from 30% to 55% by weight relative to the total weight of the granulate.

18. A granulate of gamma-hydroxybutyric acid or one of its pharmaceutically acceptable salts, consisting of:
   a solid core of a support material that represents about 21.79% by weight relative to a total weight of the granulate;
   a shell layer constituted of the gamma-hydroxybutyric acid or one of its salts that is deposited around and supported by the solid core, the gamma-hydroxybutyric acid representing about 34.57% by weight relative to the total weight of the granulate;
   a binder deposited around the solid core that represents about 5% by weight relative to the total weight of the granulate;
   a diluent that represents about 10% by weight relative to the total weight of the granulate;
   a pre-coating layer that represents about 2% by weight relative to the total weight of the granulate;
   a coating layer that represents about 21.89% by weight relative to the total weight of the granulate;
   a plasticizer that represents about 2.19% by weight relative to the total weight of the granulate;
   a lubricant that represents about 2.50% by weight relative to the total weight of the granulate; and
   a coloring that represents about 0.06% by weight relative to the total weight of the granulate,
      wherein the support material of the solid the core is different than the gamma-hydroxybutyric acid or one of its salts constituting the shell layer.

* * * * *